united States Patent [19]

Sih

[11] 4,288,617
[45] Sep. 8, 1981

[54] 13,14-DIDEHYDRO-19-OXO-PGF$_1$ COMPOUNDS

[75] Inventor: John C. Sih, Kalamazoo, Mich.

[73] Assignee: The Upjohn Company, Kalamazoo, Mich.

[21] Appl. No.: 131,973

[22] Filed: Mar. 20, 1980

Related U.S. Application Data

[62] Division of Ser. No. 25,879, Apr. 2, 1979.

[51] Int. Cl.$^3$ ............................................. C07C 177/00
[52] U.S. Cl. .................................... 562/503; 560/121; 260/404; 260/404.5; 260/408; 260/410; 260/410.5; 260/410.9 R; 260/413

[58] Field of Search ......................... 560/121; 562/503; 260/404, 404.5, 408, 410, 410.5, 410.9 R, 413

[56] References Cited

U.S. PATENT DOCUMENTS 4,054,595 10/1977 Marx et al. ........................... 560/121

Primary Examiner—Robert Gerstl
Attorney, Agent, or Firm—Robert A. Armitage

[57] ABSTRACT

The present invention provides novel 13,14-didehydro-19-oxo-PGF$_1$ compounds, which are useful for a variety of pharmacological purposes, e.g., antiasthmatic indications.

4 Claims, No Drawings

13,14-DIDEHYDRO-19-OXO-PGF$_1$ COMPOUNDS

DESCRIPTION

CROSS REFERENCE TO RELATED APPLICATION

This application is a division of Ser. No. 025,879, filed Apr. 2, 1979.

BACKGROUND OF THE INVENTION

The present invention relates to novel prostaglandin analogs. Particularly, the invention relates to prostaglandin analogs wherein the C-19 position is substituted by oxo, i.e., 19-keto-PG compounds or 19-oxo-PG compounds. Most particularly, the present invention relates to novel 13,14-Didehydro-19-oxo-PGF$_1$ compounds, a disclosure of the preparation and pharmacological use of which is incorporated here by reference from U.S. Ser. No. 025,899, filed Apr. 2, 1979.

PRIOR ART

Prostaglandins exhibiting a variety of substitution at the C-19 position are known. See particularly J. C. Sih, et al., JACS 91:3685 (1969) wherein 19-oxo-PGE$_2$ and 13,14-dihydro-19-oxo-PGE$_1$ are disclosed. Further, Chemical Abstracts 86:43265H purportedly discloses 19-oxo-PGF$_2\alpha$. The abstract is derived from Japanese Kokai No. 76 82,245.

SUMMARY OF THE INVENTION

The present invention particularly provides:
a compound of the formula

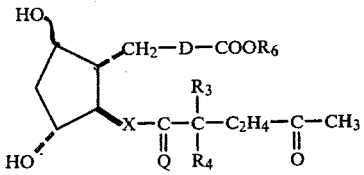

wherein D is
(1) (CH$_2$)$_3$—(CH$_2$)$_g$—CH$_2$—, or
(2) (CH$_2$)$_3$—(CH$_2$)$_g$—CF$_2$—;
wherein g is zero, one, two, or three;
wherein Q is $\alpha$-OH:$\beta$-R$_5$ or $\alpha$-R$_5$:$\beta$-OH, wherein R$_5$ is hydrogen or methyl;
wherein R$_6$ is
 (a) hydrogen,
 (b) alkyl of one to 12 carbon atoms, inclusive,
 (c) cycloalkyl of 3 to 10 carbon atoms, inclusive,
 (d) aralkyl of 7 to 12 carbon atoms, inclusive,
 (e) phenyl,
 (f) phenyl substituted with one, 2, or 3 chloro or alkyl groups of one to 3 carbon atoms, inclusive,
 (g) —(p-Ph)—CO—CH$_3$,
 (h) —(p-Ph)—NH—CO—(p-Ph)—NH—CO—CH$_3$,
 (i) —(p-Ph)—NH—CO—(p-Ph),
 (j) —(p-Ph)—NH—CO—CH$_3$,
 (k) —(p-Ph)—NH—CO—NH$_2$,
 (l) —(p-Ph)—CH=N—NH—CO—NH$_2$,
 (m) $\beta$-naphthyl,
 (n) —CH$_2$—CO—R$_{28}$,
  wherein (p-Ph) is para-phenyl or inter-para-phenylene,
  wherein R$_{28}$ is phenyl, p-bromophenyl, p-biphenylyl, n-nitrophenyl, p-benzamidophenyl, or 2-naphthyl, or
 (o) a pharmacologically acceptable cation;
wherein R$_3$ and R$_4$ are hydrogen, methyl, or fluoro, being the same or different, with the proviso that one of R$_3$ and R$_4$ is fluoro only when the other is hydrogen or fluoro; and
wherein X is —C≡C—.

The compounds of the present invention are particularly useful for inducing prostaglandin-like biological effects, as described in U.S. Ser. No. 026,066. Uses of compounds in accordance with the present invention include, therefore, antiasthmatic indications.

DESCRIPTION OF THE PREFERRED EMBODIMENTS

The present invention particularly relates to:
13,14-didehydro-19-oxo-PGF$_1\alpha$, and
13,14-didehydro-15(R)-19-oxo-PGF$_1\alpha$.

I claim:
1. A compound of the formula

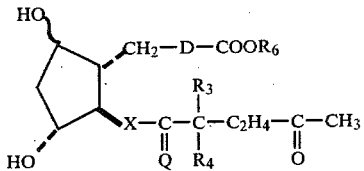

wherein D is
(1) (CH$_2$)$_3$—(CH$_2$)$_g$—CH$_2$—, or
(2) (CH$_2$)$_3$—(CH$_2$)$_g$—CF$_2$—;
wherein g is zero, one, two, or three;
wherein Q is $\alpha$-OH:$\beta$-R$_5$ or $\alpha$-R$_5$:$\beta$-OH, wherein R$_5$ is hydrogen or methyl;
wherein R$_6$ is
 (a) hydrogen,
 (b) alkyl of one to 12 carbon atoms, inclusive,
 (c) cycloalkyl of 3 to 10 carbon atoms, inclusive,
 (d) aralkyl of 7 to 12 carbon atoms, inclusive,
 (e) phenyl,
 (f) phenyl substituted with one, 2, or 3 chloro or alkyl groups of one to 3 carbon atoms, inclusive,
 (g) —(p-Ph)—CO—CH$_3$,
 (h) —(p-Ph)—NH—CO—(p-Ph)—NH—CO—CH$_3$,
 (i) —(p-Ph)—NH—CO—(p-Ph),
 (j) —(p-Ph)—NH—CO—CH$_3$,
 (k) —(p-Ph)—NH—CO—NH$_2$,
 (l) —(p-Ph)—CH=N—NH—CO—NH$_2$,
 (m) $\beta$-naphthyl,
 (n) —CH$_2$—CO—R$_{28}$,
  wherein (p-Ph) is para-phenyl or inter-para-phenylene,
  wherein R$_{28}$ is phenyl, p-bromophenyl, p-biphenylyl, p-nitrophenyl, p-benzamidophenyl, or 2-naphthyl, or
 (o) a pharmacologically acceptable cation;
wherein R$_3$ and R$_4$ are hydrogen, methyl, or fluoro, being the same or different, with the proviso that one of R$_3$ and R$_4$ is fluoro only when the other is hydrogen or fluoro; and
wherein X is —C≡C—.

2. A compound according to claim 1, wherein R$_6$ is hydrogen or methyl.

3. 13,14-Didehydro-19-oxo-PGF$_1\alpha$, a compound according to claim 2.

4. 13,14-Didehydro-15(R)-19-oxo-PGF$_1\alpha$, a compound according to claim 2.

* * * * *